United States Patent [19]

Weiss et al.

[11] 4,024,020

[45] May 17, 1977

[54] METHOD OF CELL CULTURE ON POLYACRYLONITRILE SURFACE

[75] Inventors: Stefan A. Weiss, Bowie, Md.; John H. Johnson, Kirkwood, Mo.

[73] Assignee: Monsanto Company, St. Louis, Mo.

[22] Filed: Dec. 15, 1975

[21] Appl. No.: 640,991

[52] U.S. Cl. ............................................. 195/1.8
[51] Int. Cl.² ...................................... C12K 9/00
[58] Field of Search ................................. 195/1.8

[56] References Cited

UNITED STATES PATENTS

| | | | |
|---|---|---|---|
| 3,850,748 | 11/1974 | Cook et al. | 195/1.8 |
| 3,873,423 | 3/1975 | Munder et al. | 195/1.8 |

*Primary Examiner*—Sam Rosen
*Attorney, Agent, or Firm*—John D. Upham; Scott J. Meyer; Joseph D. Kennedy

[57] ABSTRACT

A method of culturing cells in which the cells are fixed on a polyacrylonitrile surface.

8 Claims, No Drawings

METHOD OF CELL CULTURE ON POLYACRYLONITRILE SURFACE

The present invention relates to a method for the culture of cells which grow in films and substantially in monolayers. The culture of cells in monolayers is well known, but varying results are obtained with different surfaces employed as a substrate for such culture. Certain cells can grow in suspension in various media, while others must be attached to a surface for growth, particularly mammalian cells such as normal mammalian cells. The present invention is particularly concerned with cells which must be attached to a surface for growth, especially those which grow in films and substantially in monolayers. The invention can be utilized for the homogeneous cultivation of primary cells and diploid cell strains.

BACKGROUND OF THE INVENTION

Numerous procedures have been developed for propagating and/or maintaining cells in vitro. One of the most common prior methods involves attaching and growing cells on the interior surfaces of glass and plastic, usually polystyrene, roller tubes and bottles. Varying results have been obtained with different surfaces, with some surfaces shown to be toxic to particular cells, and there is an interest in finding improved or alternate surfaces for cell culturing. Polystyrene and a copolymer of acrylonitrile with vinyl chloride in proportions of 40 to 60 parts acrylonitrile/vinyl chloride by weight have been demonstrated effective for attachment of a number of types of cells.

SUMMARY OF THE INVENTION

A polyacrylonitrile polymer has now been found to be particularly effective as a surface for attachment of cells for cell culturing, particularly the homopolymer of acrylonitrile or a copolymer having a very limited amount of comonomer, no more than 15% on a weight basis, i.e. acrylonitrile polymers with 85 plus percent acrylonitrile, which are considered as modified polyacrylonitriles. Polyacrylonitrile in particular tests resulted in cell attachment and very satisfactory growth where other polymer materials resulted in growth only to very low density, or no cell attachment. The invention is of particular interest for the culture of differentiated cells, such as primary cells from differentiated tissue. By control of the environment, such as oxygen supply for aerobic cells, it is also an objective to utilize the present invention to maintain normal cells representative of the tissue of origin in vitro, with reproducible growth and function.

DETAILED DISCLOSURE

The present invention involves attaching and propagating cells on polyacrylonitrile surfaces. The polyacrylonitrile is a solid high molecular weight resin obtainable by addition polymerization of acrylonitrile, alone or with very minor modifying amounts of addition polymerizable co-monomers. It has been found that polyacrylonitrile has a surface suitable for cell attachment and growth, and that this is true for the homopolymer and for polymers containing only very small amounts of other suitable monomers, but that large amounts of co-monomers tend to change the properties of the polymer with respect to supporting cell growth. Thus it is desired to utilize polymers which retain to a great extent the cell growth properties characteristic of the homopolymer of polyacrylonitrile and to use only very small amounts, such as 15% or 10% or less by weight of modifyng monomers of desired to modify certain of the physical properties of the acrylonitrile polymer. Thus acrylonitrile polymers often contain 5 to 10% by weight of vinyl acetate or vinyl halides or similar vinyl monomers, and such modified polyacrylonitriles will be considered as polyacrylonitrile for the purposes of this invention. Similarly, the present invention includes the use of polyacrylonitrile alone, or when blended with other resins, such as with up to 15% by weight of compatible polymers. As co-monomers, in addition to those named, other monomers can be used which have no toxic effect upon the desired cell growth, so that the resulting acrylonitrile copolymer will be suitable for cell attachment and growth. Ordinarily the polymers utilized will result from polymerization of acrylonitrile, but other monomers can be used and converted to have the nitrile groups after polymerization. Also polymers with some minor hydrolysis or other modifications of the nitrile group can suitably be used.

The polyacrylonitrile surfaces can be subjected to various surface treatments or other physical or chemical treatments for various purposes, and some such treatments may enhance properties for cell attachment and growth. The surfaces for the cell support can be flat or of various irregular shapes, and can be substantially continuous and impervious, or can be porous, fibrous, permeable, or otherwise discontinuous.

The cells are incubated in a nutrient cell culture medium under cell growth maintenance conditions of pH and temperature. Suitable nutrient cell culture media are known to the art and such may be used in the method of the present invention. Typically such nutrient culture media contain the known essential amino acids, vitamins, carbohydrates, mineral salts and preferably, blood serum. Fungicides and bacteriocides may also be included in such media in desired amounts to prevent the growth of undesired microorganisms. As indicated above the pH of the nutrient medium is advantageously controlled within the desired range (typically in the range of 6.8–8.2) by including small amounts of carbon dioxide in the oxygen carrier. However if desired the pH can be controlled by including a suitable buffer such as HEPES buffer (a mixture of N-2-hydroxyethyl piperazine and N'-2-ethane sulfonic acid) in the nutrient cell culture medium itself. Other suitable methods for controlling pH such as passing the medium over ionic exchange resins may also be employed.

The choice of temperature for incubation of cells is within the skill of the worker in the field of cell and tissue culturing and will depend principally upon the physiological temperature for the particular cells to be propagated, that is the optimum temperature at which growth or maintenance of the cells occurs. For example when normal mammalian cells are propagated a narrow temperature range of from about 35°–40° C is typically employed whereas, for example, if the cells are reptilian in origin lower or higher temperatures may be employed.

Suitable cells for propagation in accordance with the method of the present invention include tissue cells from vertebrate animals which are capable of attachment and growth or maintenance on a surface. Of course cells which are inherently incapable of proliferation such as erythrocytes cannot be employed in the method of this invention. Examples of such suitable cells include diploid cell lines such as WI-38 human lung fibroblasts, MRC-5 male human fetal lung fibroblasts and DBS-FRh L-2 rhesus monkey fetal lung fibroblasts; primary cells such as bovine and human anterior pituitary cells, chicken embryo, frog epithelium and rat liver; and established cell lines such as Hela human cervix (carcinoma) cells, rhesus monkey kidney cells (LLC-MK$_2$) Syrian baby hamster kidney cells (BHK-21)etc. and the like.

It will be appreciated that the above list of cells is given for illustrative purposes and that other cells from other sources including avian, mammalian, reptilian and amphibian sources including normal and abnormal cells can be propagated and maintained in accordance with the method of the present invention.

The present invention can employ any cells which attach to and grow on polyacrylonitrile surfaces, and correspondingly, any polyacrylonitrile surface suitable for such attachment and growth can be employed, including modified polyacrylonitriles in which the modifying monomer is present only in small amount as discussed herein, and does not prevent such attachment and growth.

With further regard to application of the present invention, attention is directed to a commonly assigned copending application of Jacques J. Delente, Ser. No. 376,038 filed July 2, 1973, involving culturing of cells on hollow fibers with provision of air or other oxygen containing media through the fibers, and polyacrylonitrile as taught herein can be utilized for the fiber surfaces in the procedure of the said application. Also the nutrient media and other growth conditions from the said application can be utilized in the present invention.

The following examples are illustrative of the invention.

EXAMPLE 1

Hep-2 cells were cultured on a polyacrylonitrile surface as follows. Pieces of a polyacrylonitrile membrane were sterilized by autoclaving with distilled water. The pieces (16 mm × 16 mm) were placed in a tissue culture flask (75 cm$^2$), with 4 pieces per flask. Hep-2 cells at a concentration of 3 × 10$^5$/ml in a growth medium were innoculated into the flasks. The total volume of medium per flask was 15 ml. and the medium was Basal Medium Eagle's with 10% by volume fetal calf serum. The flasks were incubated for 72 hours at 37° C. The flasks were observed under a 100 power microscope and the pieces of polyacrylonitrile membrane were covered confluently with Hep-2 cells. No cytotoxicity was observed in the cell monolayers. Pieces of the membrane were removed from the flasks with forceps and transferred into petri dishes and potomicrographed to shown cell attachment. The acrylonitrile polymer used in the foregoing procedure was a blend composed mainly of an acrylonitrile copolymer (88 parts by weight) with a small amount of vinyl acetate, blended with a small amount of a copolymer (12 parts by weight) of acrylonitrile with monovinyl-pyridine. Acrylonitrile and vinyl acetate were in 95 to 5 weight ratio, and acrylonitrile and monovinyl pyridine in 50 to 50 weight ratio. The Hep-2 cells similarly attached to hollow fibers of the same acrylonitrile polymer blend when innoculated in the same manner.

Hep-2 cells for culturing in the foregoing procedure can be provided by removing the growth medium from a culture of the cells in a flask, "trypsinizing" the culture to remove it from the bottom of the flask by adding an 8 ml solution of 0.25% trypsin in a phosphate buffered salts solution to the monolayer to loosen it, neutralizing with 2 volumes of Basic Medium Eagle's growth medium, centrifuging, decanting the trypsin, and suspending in 20 ml of Basal Medium Eagle's.

EXAMPLE 2

Diploid cell line WI-38 derived from human embryonic lung was cultured on strips and fibers of polyacrylonitrile polymer as follows. Strips and pieces of hollow fibers of the acrylonitrile material described in Example 1 were utilized. The strips or fibers were placed in siliconized pyrex petri dishes 15 × 60 mm in diameter. The material generally stuck closely to the bottom of the dishes in the presence of added medium. Seven ml. of a WI-38 cell suspension at 1.3 × 10$^4$ cells per ml was innoculated into each dish. The medium was Eagles Minimum Essential Medium (Spinner) with 10% fetal calf serum. A National Cancer Tissue Culture media, NCTC-135 can be used as an alternate, being used with 10% fetal calf serum. The dishes were incubated at 37° C with 95% air and 5% carbon dioxide in a humidified atmosphere. After 24 hours, the dishes were examined with an inverted microscope with 125 × magnification. There was attachment and growth on the pieces of acrylonitrile polymer membrane and hollow fibers. Incubation was continued for six days and continuous growth was observed with no evidence of toxicities. The WI-38 diploid cell line cultured in the present procedure is a cell line which is "diploid" in the usual sense, i.e. at least 75% of the cells have the same karyotype as the normal cells of the derived species. The WI-38 line is recognized as derived from normal nonmalignant tissue, and as not producing tumors when injected into an animal. The cell-line is commonly utilized to establish performance of cell culture systems.

EXAMPLE 3

Anterior calf pituitary cells were cultured on acrylonitrile polymer membrane in accordance with the following procedure. Strips of acrylonitrile polymer membrane were placed in 70% ethyl alcohol for 30–45 minutes at room temperature. The strips were then transferred to a Hanks Balanced Salt Solution with phenol red and 150 units penicillin and 150 mg streptomycin per ml. After standing several hours at room temperature the strips were transferred to 30 × 15 mm petri dishes and circular, glass rings (2 mm in height) were placed on the strips to provide a means to control fluid level. A medium containing 7 ×10$^4$ anterior calf pituitary cells per ml was placed on the membrane strips, the medium being Basal Medium Eagles with double concentration of amino acids and vitamins, and containing 10% by volume fetal calf serum. The dishes were incubated at 37° C in humidified atmosphere of 96.5% air plus 3.5% carbon dioxide by volume. Photomicrographs were taken and mounted on slides. Tests were continued for fifteen days, with change of media on the sixth day. The anterior calf pituitary cells in these tissue culture procedures attached and proliferated on the acrylonitrile membranes. In similar tissue cultures in which the acrylonitrile membrane had been sterilized by steam, the pituitary cells attached and proliferated, but not as well as in the above-described procedure where the membranes had been sterilized by alcohol followed by Hanks solution. The latter type of sterilization is less apt to cause shrinkage or brittleness of an acrylonitrile polymer membrane than is heat sterilization.

Medium for preparing calf pituitary cells for use in the above procedure can be prepared by recognized techniques, for example, as follows. A calf-pituitary obtained by dissection from a freshly killed calf was stored in phosphate buffered saline solution at about 25° C. The anterior portion was dissected, cleaned to remove connective tissue, and minced. The minced anterior gland was gently mixed with an aqueous solution of trypsin in a Petri dish and allowed to stand for 20 hours to obtain release of individual cells into the fluid. The aqueous trypsin solution was prepared by mixing 10 milliliters of phosphate buffered saline solution with 250,000 units of dry powdered trypsin enzyme sold under the name Tryptar by Armour and Co., and .28 ml of 0.5 normal sodium hydroxide to give a pH of 7.2 The cells in the trypsin solution were innoculated with about 10 ml of Basal Medium Eagles with calf serum, about pH 6.9, and the diluted Tryptar was poured off, and 10 ml of the Basal Medium Eagles (with calf serum) was added and the material was dissociated with gentle pipetting until particles were dissolved. The suspension was filtered through gauze and the gauze washed with medium, and the filtrate was diluted to about 25 ml.

EXAMPLE 4

A sample of polyacrylonitrile particles suspended in water was obtained. The polymer had been prepared by free radical catalyzed polymerization of acrylonitrile. The polymer was washed by suspension in boiling water. "Fines" were removed by suspension and settling from water, and the polymer was washed with distilled water, followed by 0.85% saline solution. The polymer material was centrifuged, resuspended, autoclaved at 121° C in a sample bottle, centrifuged, aspirated, and resuspended in 25 ml of Dulbecco's modified Eagle Medium with 10% by weight fetal calf serum (Dulbecco's MEM Powder, Cat. No. H-16 from Grand Island Biological Company is suitable). The material was centrifuged and resuspended several times and additional medium added to obtain desired polymer concentrations of 10%, 5% and 1% by weight. 4 ml amounts of the polyacrylonitrile suspension were added to separate 60 mm plastic (Falcon polystyrene) petri dishes. Cells, SV3T3, were removed by trypsination from a culture, centrifuged and re-suspended in Dulbecco's medium with 10% fetal calf serum. One ml of the cell suspension was used to innoculate each polyacrylonitrile suspension, and also to innoculate controls with no polyacrylonitrile present.

The petri dishes were placed in an incubator (5% by volume carbon dioxide to 95% by volume air) at 37° C. After two days, the petri dishes were removed for fixation and staining. The medium was then removed from each dish and the dish washed with 0.85% saline solution which was added to the removed medium. The solutions were centrifuged and the solids were re-suspended in buffered 5 ml 10% by weight formaldehyde solution and allowed to stand for one-half hour. A 1% crystal violet solution, 2 drops, was added and after 10 minutes for staining the solids were washed and resuspended in 1 ml distilled water and prepared for observation under the microscope. Many cells were observed to be attached to the polyacrylonitrile particles. The petri dishes from the incubation from which the medium had been removed were similarly fixed and stained, and it was noted that no cells were attached to the bottom of the dish which had contained a 10% suspension of polyacrylonitrile particles, while the dishes from the 1% suspension and the controls were 100% confluent with cells. The cells had greater affinity for the polyacrylonitrile than for the polystyrene of the petri dishes. Media from the 10% polyacrylonitrile suspensions was acid, indicating cell growth or metabolism.

Media containing polyacrylonitrile particles was incubated for two days and the media was then added to control petri dishes confluent with cells, and two days later no evidence of cytotoxicity was observed and the cell layer looked as good as a control which had been innoculated with fresh Dulbecco's medium with fetal calf serum.

Petri dishes with cell-innoculated polyacrylonitrile particle suspensions and controls which had been incubated as above were utilized for determination of cell count. Media were removed and centrifuged, and the dishes were trypsinized and the trypsin solutions added to re-suspend the corresponding solid pellet from centrifuging. The petri dishes were further washed, and the washings added to the suspensions, which were then pipetted and decanted through a guaze pad for the purpose of removing polymer particles while permitting losened cells to go through. The cell suspensions were centrifuged and resuspended and counted. With the initial innoculum estimated as 1 to $4 \times 10^6$ cells per plate, the dish from the 10% suspension of polyacrylonitrile particles yielded $1.045 \times 10^7$ cells per plate, the 5% suspension yielded $1.58 \times 10^7$ cells per plate, the 1% suspension yielded $1.523 \times 10^7$ cells per plate, and a control with no particles yielded $2.784 \times 10^7$ cells per plate. The SVT3 cells grow on polyacrylonitrile particles and will attach to sufficient polyacrylonitrile particles in preference to polystyrene.

In similar procedures to the above, the SV3T3 cells attached well to two grades of cellulose acetate butyrate, but the cell densities were only 10–20% of those with polyacrylonitrile. For other polymers, including a polyvinyl chloride, the cells exhibited little or no affinity, showing a greater affinity for the polystyrene surface of the culture vessel.

The SV3T3 cells were mouse embryonic fibroblasts of the well known established line having such designation; see Todaro et al, Journal of Cell Biology, Vol. 17, page 299 (1963); Pathology, Vol. 54, page 66 (1964). The cells were employed as a type of anchorage dependent mammalian cells which grow in monolayers. The nutrient media and other culturing conditions described in such publications are also suitable for use in the present invention.

Polymeric films were prepared by casting from 10% solids in dimethyl sulfoxide with a Gardner Knife at a 20 mil setting. The films were then immersed in distilled water and washed for 24 hours. Discs were cut from the films and placed on plastic tissue culture plates and held there by plexiglass rings. The materials were washed and sterilized. A culture of SV3T3 cells was treated with 10 ml of phosphate buffer solution with calcium and magnesium salts and ethylene diamine tetraacetic acid, and a medium prepared containing the cells which was used to innoculate the plates, with 0.5 ml containing $2.645 \times 10^5$ cells being used per plate. An additional 2 ml of fresh medium was then added to each plate. The plates were incubated with change of medium every two days. After 5 days, the cells appeared insufficient, so an additional 0.5 ml of suspension of $1.04 \times 10^6$ cells/ml was added to each plate. The viable count approximated 72%. The medium was changed every other day, and harvested after seven days. The DNA (deoxyribonucleic acid) per plate was determined as an assay of cell growth and attachment. With the tissue culture dish control having 140 micrograms DNA, the membranes were rated for relative efficiency compared to the tissure culture dish, with an acrylonitrile polymer having a 71% rating, and the same polymer with some hydrolysis (to provide hydrophilic groups), a 65% rating. The acrylonitrile polymer blended (88:12) with a 50:50 copolymer of acrylonitrile/vinyl pyridine had a 46% rating. An acrylonitrile vinyl chloride copolymer (39.7:60.3) had a 39% rating, which was similar to the 37% rating for another acrylonitrile/vinyl chloride polymer, 40:60 by weight Amicon XM-50 (sample containing some blue dye). Cellulose acetate had a 28% rating. The acrylonitrile polymer referred to above was a copolymer of 95% acrylonitrile with 5% vinyl acetate, the percentages being by weight.

The present invention will be useful for the production of cells to be harvested and re-cultured for various purposes, or for culturing cells for production of hormones or other cellular products, or for use in assay or other procedures, or in production of vaccines or various viral or anti-viral materials. While there can be variations in the production of cells, the procedures will often involve aseptically implanting the cells in a nutrient tissue culture medium in contact with the polyacrylonitrile causing attachment of cells thereto, incubating, releasing the cells from the surface, agitating to disperse the cells into small aggregrates, and harvesting the cells.

What is claimed is:

1. In a method for culture of the type of cells which grow attached to a surface, the improvement comprising fixing the cells to be cultivated to a polyacrylonitrile surface maintained in contact with a nutrient culture medium, said polyacrylonitrile comprising acrylonitrile with 0 to 15% by weight of comonomer.

2. The method of claim 1 in which the cells are mammalian cells.

3. The method of claim 1 in which the cells are diploid cells.

4. The method of claim 1 in which the cells are normal human cells.

5. The method of claim 1 in which the surface is a homopolymer of acrylonitrile.

6. A method for propagating or maintaining cells in vitro which comprises providing a suspension of cells in a culture medium and contacting such medium with a polymeric surface suitable for cell attachment and growth which is a polymer of acrylonitrile with up to 15% by weight of a vinyl comonomer, and incubating under cell growth or maintenance conditions of pH and temperature.

7. The method of claim 6 in which the polymer is a copolymer of acrylonitrile and vinyl acetate.

8. The method of claim 7 in which the polymer is a copolymer of about 95% by weight acrylonitrile and 5% by weight vinyl acetate.

* * * * *